(12) United States Patent  (10) Patent No.: US 7,865,008 B2
Graessle et al.  (45) Date of Patent: *Jan. 4, 2011

(54) BIOLOGICAL GROWTH PLATE SCANNER WITH AUTOMATED INTAKE

(75) Inventors: Josef A. Graessle, Kaarst (DE); Kevin R. Green, Maplewood, MN (US); Albert Vent, Eschweiler (DE)

(73) Assignee: 3M Innovative Properties Company, St. Paul, MN (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/365,572

(22) Filed: Feb. 4, 2009

(65) Prior Publication Data

US 2010/0232660 A1   Sep. 16, 2010

Related U.S. Application Data

(62) Division of application No. 10/655,328, filed on Sep. 4, 2003, now Pat. No. 7,496,225.

(51) Int. Cl.
  *G06K 9/00* (2006.01)
  *G01N 21/00* (2006.01)
  *C12M 1/34* (2006.01)
(52) U.S. Cl. ............... 382/133; 422/63; 435/287.3
(58) Field of Classification Search ............... 382/128, 382/129, 130, 131, 132, 133, 134, 321; 435/287.3, 435/288.7; 436/63, 519; 600/443, 444, 445, 600/446, 447; 623/2, 13, 20.17, 917, 23.49; 378/12, 98.6, 137
See application file for complete search history.

(56) References Cited

U.S. PATENT DOCUMENTS

| | | |
|---|---|---|
| 3,493,772 A | 2/1970 | Daughters et al. |
| 3,745,090 A | 7/1973 | Chappelle et al. ........... 195/103 |
| 3,811,036 A | 5/1974 | Perry |
| 3,962,040 A | 6/1976 | Campbell et al. |
| 4,118,280 A | 10/1978 | Charles et al. |

(Continued)

FOREIGN PATENT DOCUMENTS

DE   19819144   4/1998

(Continued)

OTHER PUBLICATIONS

Decision on Appeal dated Dec. 2, 2008 in U.S. Appl. No. 10/306,663, filed Nov. 27, 2002 (18 pgs.).

(Continued)

*Primary Examiner*—Abolfazl Tabatabai

(57) ABSTRACT

The invention is directed to a biological scanner for scanning biological growth plates. The biological growth plate is loaded into the biological scanner via motorized rollers, and an actuator presses the growth plate against a platen once the growth plate is drawn to a scanning position within the scanner. The biological scanner then generates one or more images of the growth plate. Moreover, sensors can be arranged to facilitate sensing and positioning of the growth plate in a plurality of locations for imaging different parts of the plate. Additional embodiments are directed to features such as a hinged door that facilitates access to the scanner, and footings disposed on various sides of the scanner to facilitate flip-over of the scanner for simplified use by right-handed or left-handed users.

17 Claims, 7 Drawing Sheets

U.S. PATENT DOCUMENTS

| | | | |
|---|---|---|---|
| 4,146,775 A | 3/1979 | Kirchner et al. ............. 219/295 | |
| 4,160,601 A | 7/1979 | Frosch et al. | |
| 4,353,988 A | 10/1982 | Couse et al. | |
| 4,563,096 A | 1/1986 | Chidlow et al. ............. 356/440 | |
| 4,591,567 A | 5/1986 | Britten et al. | |
| 4,637,053 A | 1/1987 | Schalkowsky ............. 382/133 | |
| 4,720,463 A | 1/1988 | Farber et al. | |
| 4,724,215 A | 2/1988 | Farber et al. | |
| 4,817,785 A | 4/1989 | Farber et al. | |
| 4,856,073 A | 8/1989 | Farber et al. | |
| 5,117,467 A | 5/1992 | Misaki et al. | |
| 5,202,010 A | 4/1993 | Guzman ..................... 204/299 | |
| 5,270,173 A | 12/1993 | Yonemori et al. ............. 435/29 | |
| 5,290,701 A | 3/1994 | Wilkins | |
| 5,329,686 A | 7/1994 | Kildal et al. | |
| 5,364,766 A | 11/1994 | Mach et al. | |
| 5,366,873 A | 11/1994 | Eden et al. | |
| 5,372,485 A | 12/1994 | Sumser et al. | |
| 5,372,936 A * | 12/1994 | Fraatz et al. ................. 435/34 | |
| 5,375,043 A | 12/1994 | Tokunaga | |
| 5,403,722 A | 4/1995 | Floeder et al. | |
| 5,428,690 A | 6/1995 | Bacus et al. | |
| 5,448,652 A | 9/1995 | Vaidyanathan et al. | |
| 5,510,246 A | 4/1996 | Morgan | |
| 5,539,517 A | 7/1996 | Cabib et al. | |
| 5,573,950 A | 11/1996 | Graessle et al. | |
| 5,591,974 A | 1/1997 | Troyer et al. ................ 250/336 | |
| 5,671,290 A | 9/1997 | Vaidyanathan | |
| 5,694,478 A | 12/1997 | Braier et al. | |
| 5,721,435 A | 2/1998 | Troll | |
| 5,723,308 A | 3/1998 | Mach et al. | |
| 5,744,322 A | 4/1998 | Krejcarek et al. | |
| 5,747,333 A | 5/1998 | Jungmann-Campello et al. | |
| 5,781,311 A | 7/1998 | Inoue et al. | |
| 5,787,189 A | 7/1998 | Lee et al. | |
| 5,817,475 A | 10/1998 | Gibbs et al. | |
| 5,995,645 A * | 11/1999 | Soenksen et al. ............. 382/133 | |
| 6,002,789 A | 12/1999 | Olsztyn et al. | |
| 6,058,209 A | 5/2000 | Vaidyanathan et al. ...... 382/203 | |
| 6,096,272 A | 8/2000 | Clark et al. | |
| 6,107,054 A | 8/2000 | Gibbs | |
| 6,238,879 B1 | 5/2001 | Gibbs | |
| 6,243,486 B1 * | 6/2001 | Weiss .......................... 382/133 | |
| 6,271,022 B1 | 8/2001 | Bochner | |
| 6,319,668 B1 | 11/2001 | Nova et al. ..................... 435/6 | |
| 6,372,485 B1 | 4/2002 | Clark et al. | |
| 6,381,353 B1 | 4/2002 | Weiss .......................... 382/133 | |
| 6,418,180 B1 | 7/2002 | Weiss ............................. 377/6 | |
| 6,459,994 B1 | 10/2002 | Parekh et al. ................. 702/19 | |
| 6,485,979 B1 | 11/2002 | Kippenhan et al. | |
| 6,488,890 B1 | 12/2002 | Kirckof | |
| 6,642,953 B1 | 11/2003 | Nieto Velasco et al. | |
| 6,673,315 B2 | 1/2004 | Sheridan et al. | |
| 6,690,470 B1 | 2/2004 | Baer et al. | |
| 6,711,283 B1 | 3/2004 | Soenksen .................... 382/133 | |
| 6,716,588 B2 * | 4/2004 | Sammak et al. .............. 435/7.2 | |
| 6,737,266 B1 * | 5/2004 | Wicks et al. ............. 435/288.2 | |
| 6,999,607 B2 * | 2/2006 | Kiros et al. .................. 382/128 | |
| 7,057,721 B2 | 6/2006 | Gardiner, Jr. et al. ........ 356/301 | |
| 7,298,885 B2 * | 11/2007 | Green et al. ................. 382/133 | |
| 7,298,886 B2 | 11/2007 | Plumb et al. ................ 382/133 | |
| 7,496,225 B2 | 2/2009 | Graessle et al. ............. 382/133 | |
| 2001/0031502 A1 | 10/2001 | Watson, Jr. et al. | |
| 2001/0041347 A1 | 11/2001 | Sammak et al. | |
| 2002/0025082 A1 | 2/2002 | Kaushikkar et al. ......... 382/294 | |
| 2002/0064867 A1 | 5/2002 | Clark et al. | |
| 2002/0137091 A1 | 9/2002 | Luttermann et al. .......... 435/7.1 | |
| 2002/0167161 A1 | 11/2002 | Butland ......................... 283/72 | |
| 2002/0191825 A1 | 12/2002 | Parekh et al. ............... 382/128 | |
| 2004/0101189 A1 | 5/2004 | Green et al. | |
| 2004/0101951 A1 | 5/2004 | Vent et al. | |
| 2004/0101952 A1 | 5/2004 | Vent | |
| 2004/0101954 A1 | 5/2004 | Graessle et al. | |
| 2004/0102903 A1 | 5/2004 | Graessle et al. | |
| 2005/0053265 A1 | 3/2005 | Graessle et al. ............. 382/128 | |
| 2005/0053266 A1 | 3/2005 | Plumb et al. ................ 382/128 | |
| 2005/0095665 A1 | 5/2005 | Williams et al. ............... 435/34 | |
| 2005/0222778 A1 | 10/2005 | Levinson et al. .............. 702/19 | |
| 2006/0263258 A1 | 11/2006 | Harris et al. ................... 422/99 | |
| 2008/0003562 A1 | 1/2008 | Plumb et al. .................... 435/3 | |

FOREIGN PATENT DOCUMENTS

| | | |
|---|---|---|
| EP | 0 008 826 A2 | 3/1980 |
| EP | 0 088 601 A1 | 9/1983 |
| EP | 0 301 600 | 1/1989 |
| EP | 0 397 256 A2 | 11/1990 |
| EP | 0 397 256 A3 | 11/1990 |
| EP | 0 429 030 A2 | 5/1991 |
| EP | 0 429 030 A3 | 5/1991 |
| EP | 0 193 385 B1 | 7/1992 |
| EP | 0 547 709 A2 | 6/1993 |
| EP | 0 547 709 A3 | 6/1993 |
| EP | 0 819 930 A2 | 1/1998 |
| EP | 1074610 A1 | 2/2001 |
| GB | 2 249 829 A | 5/1992 |
| JP | 60-83597 | 5/1985 |
| JP | 62-215383 | 9/1987 |
| JP | 5-249105 | 9/1993 |
| JP | 6-98220 | 4/1994 |
| JP | 6-109545 | 4/1994 |
| JP | 7-275200 | 10/1995 |
| JP | 10-24283 | 1/1998 |
| JP | 10-500302 | 1/1998 |
| JP | 2000-270840 | 10/2000 |
| JP | 2001-242082 | 7/2001 |
| JP | 2002-538440 | 11/2002 |
| WO | WO 92/12233 | 7/1992 |
| WO | WO 94/01528 | 1/1994 |
| WO | WO 94/26926 | 11/1994 |
| WO | WO 95/16768 | 6/1995 |
| WO | WO95/31732 | 11/1995 |
| WO | WO 96/18721 | 6/1996 |
| WO | WO 98/53301 | 11/1998 |
| WO | WO 98/59314 | 12/1998 |
| WO | WO 99/28436 | 6/1999 |
| WO | WO 00/32807 | 6/2000 |
| WO | WO 00/49129 | 8/2000 |
| WO | WO 00/49130 | 8/2000 |
| WO | WO 00/51058 | 8/2000 |
| WO | WO 00/65094 | 11/2000 |
| WO | WO 01/09371 | 2/2001 |
| WO | WO 01/83673 A2 | 11/2001 |
| WO | WO 02/090966 | 1/2002 |
| WO | WO02/37938 | 5/2002 |
| WO | WO02/38724 | 5/2002 |
| WO | WO 02/46354 | 6/2002 |
| WO | WO 03/014400 | 2/2003 |
| WO | WO 03/038413 | 5/2003 |

OTHER PUBLICATIONS

Product brochure entitled "Powerful data handling for GLP conformance" by ProtoCOL, Synbiosis, a division of Synoptic Ltd, Cambridge, UK (4 pgs.).

Product brochure entitled "Efficient Batch Handling" by ProtoZONE, Synbiosis, a division of Synoptic Ltd., Cambridge, UK (4 pgs.).

Product brochure entitled "Petrifilm™ Information Management System—Reduce Operational Costs and Increase Productivity"; 3M Microbiology Products; 1999; 70-2009-1996-0; (3 pgs.).

Corkidi et al.; "COVASIAM: an Image Analysis Method That Allows Detection of Confluent Microbial Colonies and Colonies of Various Sizes for Automated Counting", Applied and Environmental Microbiology, vol. 64, No. 4, Apr. 1998, pp. 1400-1404.

Ilya et al.; "Streamlines Yeast Colorimetric Reporter Activity Assays Using Scanners and Plate Readers", BioTechniques, vol. 29, No. 2, Aug. 2000.

K. M. Wright et al., "Determination of Mean Growth Parameters of Bacterial Colonies Immobilized in Gelatin Gel Using a Laser Gel-Cassette Scanner", International Journal of Food Microbiology, 2000, pp. 75-89.

Gilchrist et al., "Spiral Plate Method for Bacterial Determination", Applied Microbiology, Feb. 1973, vol. 25, No. 2, pp. 244-252.

Kalasinsky, Kathryn S. et al.; "Raman Chemical Imaging Spectroscopy Reagentless Detection and Identification of Pathogens: Signature Development and Evaluation"; Analytical Chemistry; 2007; 79 (7) pp. 2658-2673.

* cited by examiner

BIOLOGICAL GROWTH PLATE SCANNER WITH AUTOMATED INTAKE

CROSS REFERENCE TO RELATED APPLICATIONS

This application is a division of U.S. patent application Ser. No. 10/655,328, filed Sep. 4, 2003 now U.S. Pat. No. 7,496,225, which is incorporated herein by reference.

FIELD

The invention relates to biological scanners for analysis of biological growth plates and detection of bacteria or other biological agents in food samples, laboratory samples, and the like.

BACKGROUND

Biological safety is a paramount concern in modern society. Testing for biological contamination in foods or other materials has become an important and often mandatory requirement for developers and distributors of food products. Biological testing is also used to identify bacteria or other agents in laboratory samples such as blood samples taken from medical patients, laboratory samples developed for experimental purposes, and other types of biological samples. Various techniques and devices can be utilized to improve biological testing and to streamline and standardize the biological testing process.

A wide variety of biological growth plates have been developed. As one example, biological growth plates have been developed by 3M Company (hereafter "3M") of St. Paul, Minn. Biological growth plates are sold by 3M under the trade name PETRIFILM plates. Biological growth plates can be utilized to facilitate the rapid growth and detection of bacteria or other biological agents commonly associated with food contamination, including, for example, aerobic bacteria, E. coli, coliform, enterobacteriaceae, yeast, mold, Staphylococcus aureus, Listeria, Campylobacter, and the like. The use of PETRIFILM plates, or other growth media, can simplify bacterial testing of food samples.

Biological growth plates can be used to enumerate or identify the presence of bacteria so that corrective measures can be performed (in the case of food testing) or proper diagnosis can be made (in the case of medical use). In other applications, biological growth plates may be used to rapidly grow bacteria or other biological agents in laboratory samples, e.g., for experimental purposes.

Biological scanners refer to devices used to scan or count bacterial colonies, or the amount of a particular biological agent on a biological growth plate, or the like. For example, a food sample or laboratory sample can be placed on a biological growth plate, and then the plate can be inserted into an incubation chamber. After incubation, the biological growth plate can be placed into the biological scanner for automated detection and enumeration of bacterial growth. Biological scanners automate the detection and enumeration of bacteria or other biological agents on a biological growth plate, and thereby improve the biological testing process by reducing human error.

SUMMARY

In general, the invention is directed to a biological scanner for biological growth plates. A biological growth plate is inserted into the biological scanner. Upon insertion of the biological growth plate, the biological scanner generates an image of the plate. Then, the amount of biological agents that appear in the image, such as a number of bacteria colonies, can be counted or otherwise determined using image processing and analysis routines performed either by the biological scanner or an external computing device, such as a desktop computer, workstation or the like. In either case, the biological scanner automates the analysis of biological growth plates.

The biological scanner incorporates an automated loading mechanism to facilitate handling and analysis of biological growth plates by the scanner. The automated loading mechanism is configured to draw the growth plate into the scanner and place the growth plate in a scanning position. In particular, the biological growth plate is loaded into the biological scanner via motorized rollers or another transport mechanism, and an actuator presses the growth plate against a platen once the growth plate is drawn to a scanning position within the scanner. The biological scanner then generates one or more images of the growth plate.

Sensors can be arranged to facilitate sensing and positioning of the growth plate in a plurality of positions to scan different parts of the growth plate. For example, a first scanning position may correspond to an indicia on the growth plate and a second scanning position may correspond to a location of biological agents on the biological growth medium. Also, a hinged door may facilitate access to the scanner, and footings disposed on various sides of the scanner may facilitate selective positioning of the scanner in an inverted orientation for simplified use by right-handed or left-handed users.

In one embodiment, the invention provides a biological scanner for scanning a biological growth medium. The scanner comprises a transport mechanism to draw the biological growth medium into the biological scanner, a platen within the biological scanner, and one or more sensors to detect when the biological growth medium is drawn to a scanning position adjacent the platen. The scanner also includes an actuator to press the biological growth medium against the platen when the one or more sensors detect that the biological growth medium is drawn to the scanning position, and an imaging device to generate an image of the biological growth medium when the biological growth medium is pressed against the platen.

In another embodiment, the invention provides a biological scanner for scanning a biological growth medium. The scanner comprises a housing and an imaging device to generate an image of the biological growth medium when the biological growth medium is within the housing. The scanner also includes a first set of footings on a first side of the housing, and a second set of footings on a second side of the housing such that the biological scanner can be positioned on either of the first or second set of footings.

In another embodiment, the invention provides a biological scanner for scanning a biological growth medium. The scanner comprises a housing formed with a hinged door, and an imaging device to generate an image of the biological growth medium when the biological growth medium is within the housing. The scanner also includes a set of rollers to draw the biological growth medium into the biological scanner, the set of rollers including a first subset of rollers disposed on the hinged door and a second subset of rollers that abut the first subset of the rollers when the hinged door is closed.

In another embodiment, the invention provides a biological scanning system comprising a biological scanner for scanning a biological growth medium. The scanner comprises a transport mechanism to draw the biological growth medium into the biological scanner, a platen within the biological scanner, one or more sensors to detect when the biological growth medium is drawn to a scanning position adjacent the platen, an actuator to press the biological growth medium against the platen when the one or more sensors detect that the biological growth medium is drawn to the scanning position, and an imaging device to generate an image of the biological growth medium when the biological growth medium is pressed against the platen. The system also includes a computer coupled to the biological scanner and including a processor that counts biological agents in the medium based on the image.

In another embodiment, the invention provides a method comprising receiving a biological growth medium in a biological scanner, drawing the biological growth medium to a first scanning position within the scanner and generating a first image of the biological growth medium. The method also includes drawing the biological growth medium to a second scanning position within the scanner, and generating a second image of the biological growth medium.

Various aspects of the invention may provide a number of advantages. For example, the invention may ensure that a biological growth plate can be inserted into a biological scanner, properly positioned within the scanner, imaged or otherwise scanned to identify or enumerate amounts of biological agents, and then ejected from the biological scanner in an automated fashion. In particular, the sensor configurations described herein can automate the insertion and positioning of biological growth plates in a manner that ensures that reliable imaging can occur, thereby improving the integrity of automated scanning of such biological growth plates. Automation of the ejection of the plate from the biological scanner can also simplify the process for a user.

In addition a hinged door can allow for simplified access to the interior of the scanner. Accordingly, the scanner components can be cleaned or repaired with greater ease. Also, a hinged door allows for simplified alleviation of jams or other problems within biological scanner. In addition, footings disposed on various sides of the scanner provide flexibility in terms of the input and output locations of the scanner. A user, for example, may position the scanner on a given set of footings based on the users preferences or the work environment in which the scanner is used.

Additional details of these and other embodiments are set forth in the accompanying drawings and the description below. Other features, objects and advantages will become apparent from the description and drawings, and from the claims.

DETAILED DESCRIPTION

Figure 1:
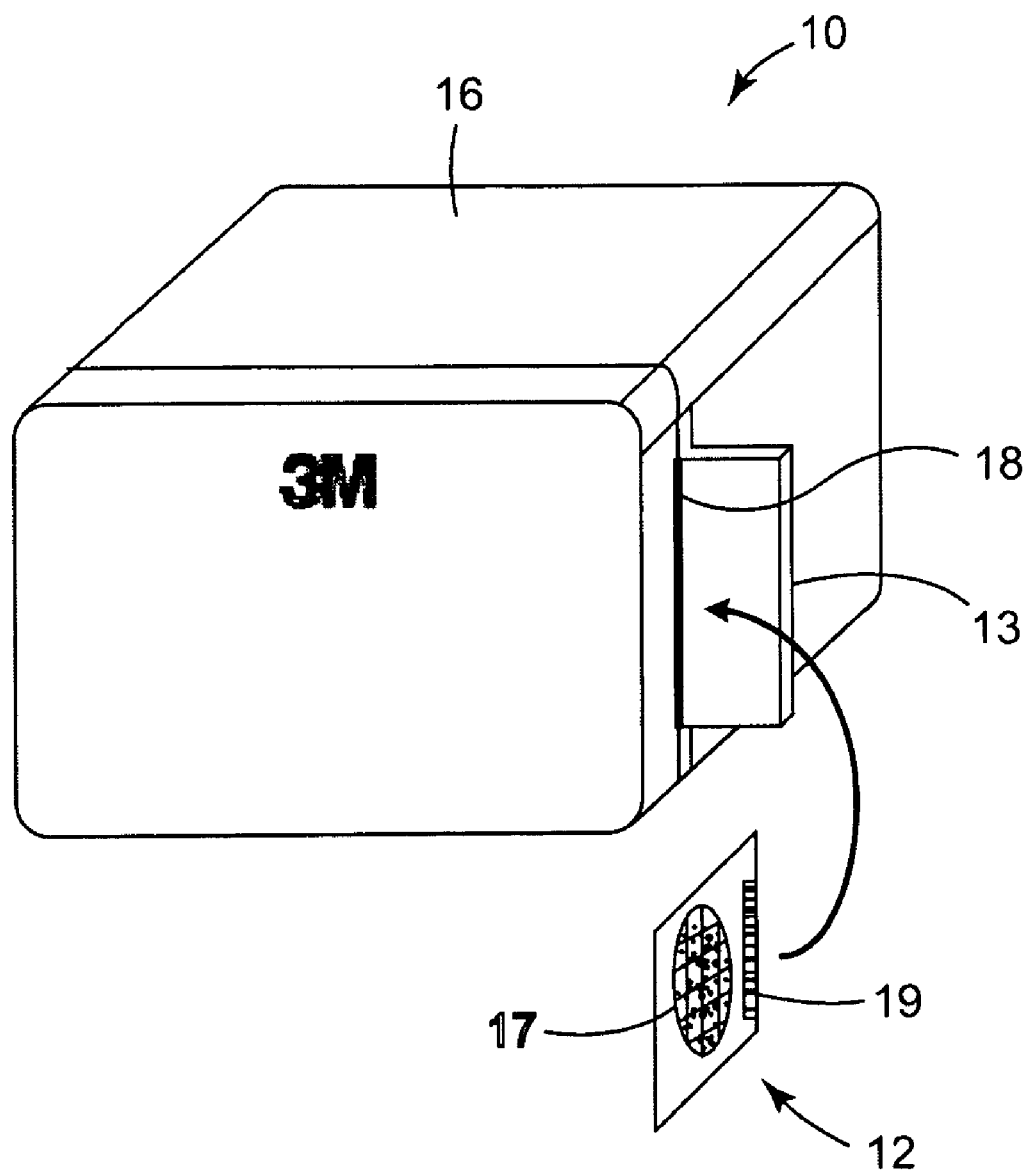
FIG. 1 is a perspective view of a biological scanner according to one embodiment of the invention.

The invention is directed to a biological scanner for biological growth plates, or other biological growth media. In accordance with the invention, the biological growth plate is loaded into the biological scanner via motorized rollers or another transport mechanism, and an actuator presses the growth plate against a platen once the growth plate is drawn to a scanning position within the scanner. The biological scanner then generates one or more images of the growth plate. An imaging device such as a 2-dimensional monochromatic camera can be positioned within the scanner to generate one or more images of the growth plate when the growth plate is pressed against the platen.

Sensors can be arranged to facilitate sensing and positioning of the growth plate in a plurality of locations for imaging different parts of the growth plate. For example, the growth plate may be sensed and imaged at a first location to generate an image of indicia, such as a bar code, on the growth plate. The indicia may identify the plate or type of plate, so that appropriate scanning and image processing routines can be selected. For example, different processing routines may be performed to count biological growth on the growth plate based on the indicia. In any case, the growth plate can be moved to a second location to generate one or more images of the biological agents on the growth plate. An arrangement of sensors automate the positioning and movement of the growth plate through the scanner. Alternatively, the imaging device could be used to detect positioning of the growth plate, instead of sensors.

Also described is a hinged door of a biological scanner that facilitates access to the interior of the scanner. A subset of the rollers can be disposed on the hinged door, such that the rollers on the door contact other rollers when the door is closed. A motor drives at least some of the rollers to draw the growth plate through the scanner.

In addition, footings may be disposed on various sides of the scanner to facilitate flip-over of the scanner for simplified use by right-handed or left-handed users In particular, footings can be disposed on various sides of the scanner to facilitate flexibility in terms of the input and output locations of the scanner. A user may position the scanner on a given set of footings based on the users preferences or the work environment in which the scanner is used.

Various aspects of the invention may be useful with a variety of biological growth plates. For example, the invention may be useful with different plate-like devices for growing biological agents to enable detection and/or enumeration of the agents, such as thin-film culture plate devices, Petri dish culture plate devices, and the like. Therefore, the term "biological growth plate" will be used broadly herein to refer to a medium suitable for growth of biological agents to permit detection and enumeration of the agents by a scanner. Many types of growth plates or media could also be used in accordance with the invention.

FIG. 1 is a perspective view of a biological scanner 10 in accordance with one embodiment of the invention. As illustrated, biological scanner 10 is designed to receive a biological growth plate 12. In particular, biological scanner 10 includes a housing 16 that defines an input slot 18 for receiving biological growth plate 12. A guide mechanism 13 may be formed on housing 16 to aid insertion of biological growth plate 12 into biological scanner 10. Biological scanner 10 also includes an ejection slot (not shown), through which growth plate 12 is ejected following imaging of growth plate 12.

Biological scanner 10 may also include other features, such as a display screen (not shown) to display the progress or results of analysis of the biological growth plate to a user. In some embodiments, biological scanner 10 includes an internal processor for analyzing the images of growth plate 12. In other embodiments, however, the processing of images occurs external to biological scanner 10, e.g., in a desktop computer, workstation, or the like. In the latter case, biological scanner 10 may include an interface to allow biological scanner 10 to be communicatively coupled to another computer.

Biological scanner 10 houses an imaging device, such as a 2-dimensional monochromatic camera for generating one or more images of an inserted biological growth plate 12. In addition, biological scanner 10 may house various illuminators for illuminating the front and back of biological growth plate 12 during imaging. The illuminators can illuminate biological growth plate 12 with one or more colors, and one or more images of growth plate 12 can be generated and then analyzed to determine bacteria counts on growth plate 12.

Growth plate 12 may include a growth area 17 where bacteria or other agents manifest on growth plate 12. Growth area 17 may be a flat surface or a recessed well. A determination of whether a given sample being tested in growth plate 12 is acceptable, in terms of bacterial colony counts, may depend on the number of bacterial colonies per unit area. Accordingly, images generated by biological scanner 10 can be used to quantify the amount of bacterial colonies per unit area on plate 12. The surface of biological growth plate 12 in growth area 17 may contain one or more growth enhancing agents designed to facilitate the rapid growth of one or more types of bacteria or other biological agents. In some cases, biological growth plate 12 is incubated prior to insertion into biological scanner 10.

Growth plate 12 may also include indicia 19, such as a bar code or other type of identification marking used to identify growth plate 12. For example, indicia 19 may identify the type of bacteria or biological agent being grown and tested on growth plate 12. Biological scanner 10 can be designed to draw growth plate 12 into scanner to a first location and generate an image of indicia 19, and then draw growth plate 12 to a second location and generate an image of growth area 17. In this manner, images of indicia 19 and growth area 17 can be generated by biological scanner 10. Alternatively, a single image may capture both indicia 19 and the growth area 17. In either case, scanning indicia 19 can facilitate identification of the type of plate being used and scanning growth area 17 and thereby improve automated counting of biological agents grown on plate 12.

By way of example, growth plate 12 may comprise a biological growth plate sold by 3M under the trade name PETRIFILM plates. Growth plate 12 can be utilized to facilitate the rapid growth and detection of bacteria or other biological agents commonly associated with food contamination, including, for example, aerobic bacteria, *E. coli*, coliform, enterobacteriaceae, yeast, mold, *Staphylococcus aureus, Listeria, Campylobacter*, or the like.

Figure 2:
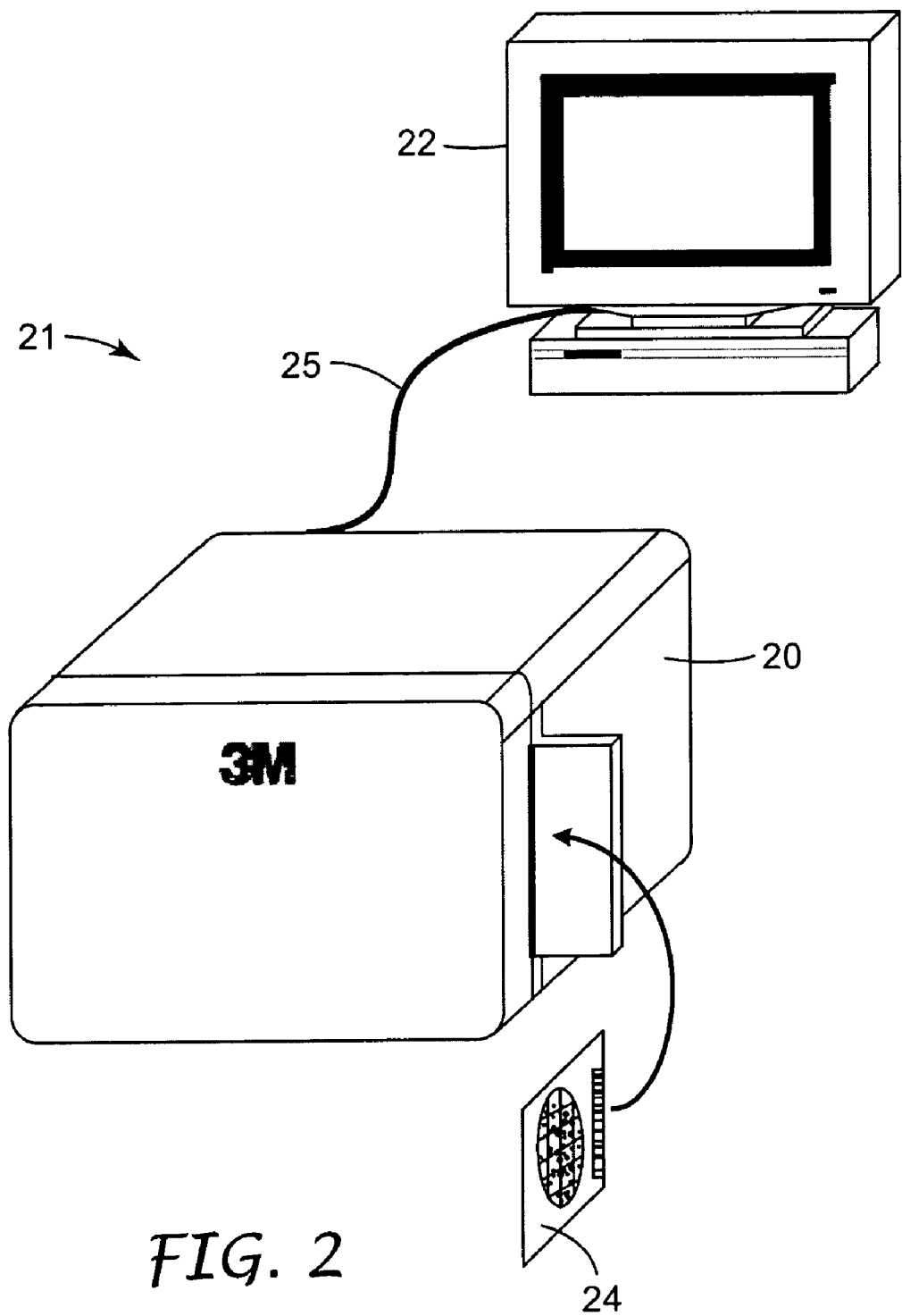
FIG. 2 is a perspective view of an exemplary system comprising a biological scanner coupled to an external computer which performs imaging analysis of the images generated by the biological scanner.

FIG. 2 is a perspective view of an exemplary system 21 comprising a biological scanner 20 coupled to an external computer 22 which performs imaging analysis of the images generated by the biological scanner. External computer 22 may include, for example, a microprocessor programmed for image analysis of biological growth plate 24. External computer 22 may comprise a personal computer (PC), desktop computer, laptop computer, handheld computer, workstation, or the like. For example, software programs can be loaded on external computer 22 to facilitate image analysis of images of biological growth plate 24 generated by biological scanner 20.

Biological scanner 20 is coupled to external computer 22 via interface 25. Interface 25, for example, may comprise a Universal Serial Bus (USB) interface, a Universal Serial Bus 2 (USB2) interface, an IEEE 1394 FireWire interface, a Small Computer System Interface (SCSI) interface, an Advance Technology Attachment (ATA) interface, a serial ATA interface, a Peripheral Component Interconnect (PCI) interface, a conventional serial or parallel interface, or the like.

Figure 3:
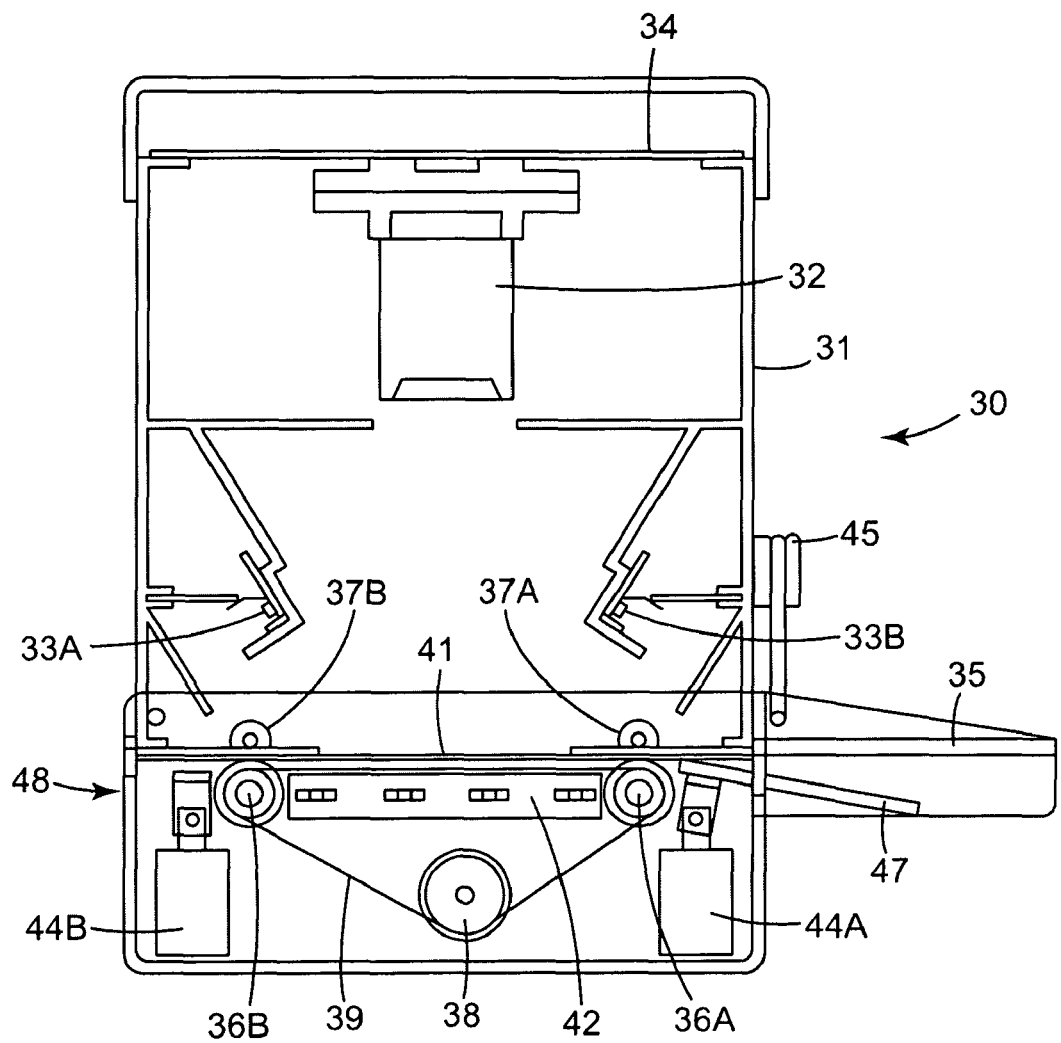
FIG. 3 is a cross-sectional top view of a biological scanner according to an embodiment of the invention.

FIG. 3 is a cross-sectional top view of a biological scanner 30, which may correspond to biological scanner 10 or biological scanner 20. As shown in FIG. 3, biological scanner 30 comprises a housing 31 that houses an imaging device 32, such as a camera and one or more illuminators 33A, 33B for illuminating a growth plate to be imagined. Circuitry 34 controls imaging device 32 and illuminators 33 in order to generate one or more images of a growth plate.

By way of example, imaging device 32 may comprise a 2-dimensional monochromatic camera and illuminators 33 may comprise three-color illuminators that selectively illuminate the growth plate with one or more colors. Various monochromatic images of the growth plate can be generated by imaging device 32 when the growth plate is illuminated by the one or more colors.

Housing 31 defines a guiding mechanism 35 to aid insertion of growth plates into biological scanner 30. A user, for example, may insert a growth plate between guiding mechanism 35 and actuator 47, which typically includes a pressure plate and may also include various back illuminators. Actuator 47 is solenoid driven to press and release the growth plate against a platen 41. When pressed against platen 41, the growth plate is positioned in the focal plane of imaging device 32. Various motorized rollers can grasp the growth plate and draw the growth plate into biological scanner 30 for imaging.

In particular, biological scanner 30 includes a set of rollers 36A, 36B, 37A, 37B which draw the growth plate into biological scanner 30 and automate movement of the growth plate through scanner 30. Other types of transport mechanisms could also be used, however, instead of rollers. In the exemplary embodiment illustrated in FIG. 3, a first subset of rollers 36A, 36B may comprise segmented rubber rollers driven by motor 38 via belt 39. Motor 38 may comprise a direct current (DC) motor responsive to sensors that detect positioning of the growth plate. In this manner, rollers 36A, 36B are motor-driven to facilitate automated movement of a growth plate through scanner 30.

A second subset of rollers 37A, 37B may comprise spring loaded pressure rollers that abut rollers 36A, 36B and provide a bias force such that a growth plate can be drawn between the set of rollers 36A, 36B, 37A, 37B by movement of subset of rollers 36A, 36B. Spring loaded rollers 36A, 36B, for example, may provide an amount of spring bias that accommodates different growth plates of different widths. Also the set of rollers 36A, 36B, 37A, 37B may be positioned sufficiently close to one another to ensure that the smallest desired growth plate can be drawn through scanner 30. Again, rollers 36A, 36B, 37A, 37B generally comprise one type of transport mechanism that may be used in accordance with the invention. However, other types of transport mechanisms could alternatively be used.

Biological scanner 30 comprises a platen 41 and an actuator 47 that presses a biological growth plate against platen 41 when the biological growth plate is positioned in a desirable scanning position. In particular, actuator 47 can press the growth plate against platen 41 to ensure the growth plate is in the focal plane of imaging device 32. Rollers 36A, 36B, 37A, 37B can draw the growth plate to the desired scanning position and actuator 47 can press the growth plate against platen 41. Illuminators 33A, 33B illuminate the growth plate with one or more colors and one or more images are generated by imaging device 32. A set of sensors (not shown in FIG. 3) can automate the detection and positioning of the growth plate at the desired scanning position. Alternatively, imaging device 32 could be used to detect positioning of the growth plate, instead of sensors.

Actuator 47 may comprise another platen such that when actuator 47 presses the growth plate against platen 41, the growth plate is sandwiched between two platens. Additional back illuminators 42 can provide back illumination to the growth plate during imaging. In some cases, back illuminators 42 are disposed on a platen that forms part of the actuator. In that case, actuator 47 further includes a three color illumination system, which may incorporate red, green and blue (RGB) illumination LEDs. The RGB LEDs may provide side illumination to actuator 47 and thereby provide back illumination to a biological growth plate that rests between actuator 47 and platen 41. In addition, similar RGB illumination LEDs may be used to provide top illumination. In other words, illuminators 33A, 33B may also comprise RGB illumination LEDs.

Actuator 47 may be solenoid driven. In that case, actuator, 47 comprises one or more solenoids 44A, 44B that cause movement of actuator 47. For example, solenoids 44A, 44B may be disposed on opposing sides of back illuminators 42 to press both sides of a growth plate against platen 41. Once the biological growth plate is positioned at a desired location one or both of solenoids 44A, 44B cause actuator 47 to press the growth plate against platen 41. Illumination and imaging is then be performed. Again, a sensor arrangement facilitates detection of the growth plate at one or more desirable locations within biological scanner 30. In one example, actuator 47 is spring biased against platen, and solenoids 44A, 44B engage to overcome the spring bias. In other words, one or both of solenoids 44A, 44B may disengage to cause actuator 47 to press against platen 41, and engage to cause actuator 47 to release from platen 41.

Upon illumination, imaging device 32 captures one or more images of the biological growth plate and provides the image(s) to a processor for analysis. The processor may be housed within biological scanner 30 or may be an external processor within another computer such as a desktop computer or workstation. In one example, imaging device 32 comprises a monochromatic imaging device that captures monochromatic images of the biological growth plate. For example, the biological growth plate may be illuminated by one or more red LEDs, at which time imaging device 32 generates a first image. Then, the biological growth plate may be illuminated by one or more green LEDs, at which time imaging device 32 generates a second image. Finally, the biological growth plate may be illuminated by one or more blue LEDs, at which time imaging device 32 generates a third image.

The processor (either internal to scanner 30 or external) receives the monochromatic images and performs analysis on the images in order to generate a bacterial colony count. The use of a monochromatic imaging device 32 to generate one or more separate monochromatic images may improve image resolution for each color, and at the same time, can reduce implementation costs associated with imaging device 32. The different images may also be combined by the processor for viewing or analysis purposes.

In some embodiments, scanner 30 may process images of different biological growth plates according to different image processing profiles. The image processing profiles may be selected based on user input or identification of the type of biological growth plate presented to scanner 30. The image processing profile may specify particular image capture conditions, such as illumination intensities, exposure durations, and colors, for capturing images of particular plate types. Thus, the scanner may apply different image capture conditions, including different illumination conditions, in processing images of different biological growth plates. Moreover, identification of an indicia on the growth plate may allow for selection of image processing profiles in an automated fashion.

As an illustration, some types of biological growth plates may require illumination with a particular color, intensity and duration. In addition, some biological growth plates may require only front or back illumination, but not both. For example, an aerobic count plate may require only front illumination as well as illumination by only a single color such as red. Alternatively, an *E. coli*/Coliform plate may require only back illumination and a combination of red and blue illumination. Similarly, particular intensity levels and durations may be appropriate. For these reasons, illumination may be controlled in response to image capture conditions specified by an image processing profile, which may be identified by the indicia 19 on growth plate 12.

After the growth plate has been scanned, rollers 36A, 36B, 37A, 37B can eject the growth plate from ejection slot 48. Another growth plate may then be inserted into biological scanner 30.

Figure 4:
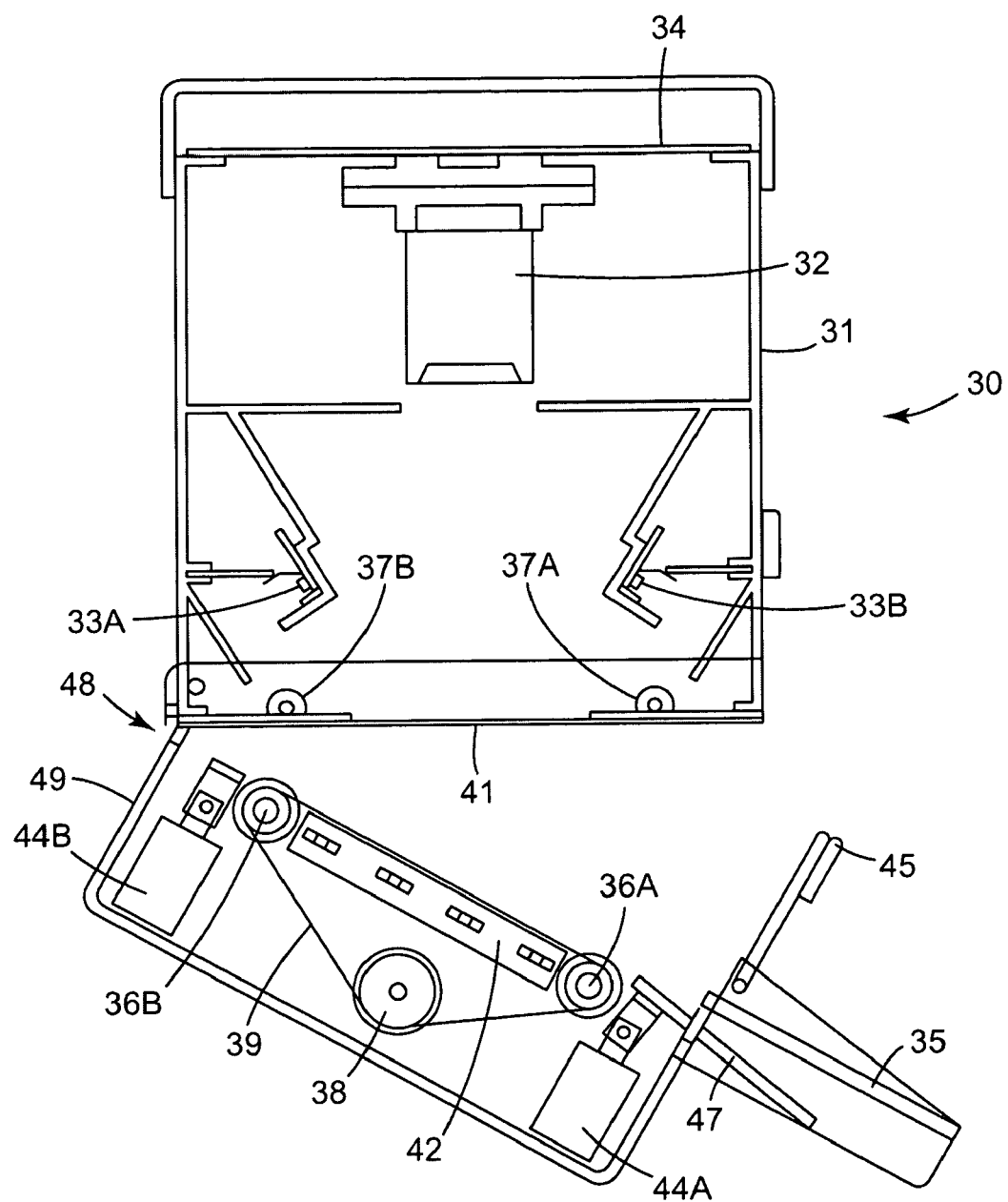
FIG. 4 is another cross-sectional top view of the biological scanner illustrated in FIG. 3.

FIG. 4 is another cross-sectional top view of biological scanner 30. As shown in FIG. 4, housing 31 may define a hinged door 49 that can be fixed in a closed position via locking mechanism 45. Hinged door 49 facilitates easy access to the interior of biological scanner 30. Accordingly, cleaning and maintenance of various components of biological scanner 30 can be performed by opening door 49 as shown in FIG. 4. Also, hinged door 49 can be useful for providing access to alleviate jams or other problems within biological scanner 30.

Rollers 36A, 36B, motor 38, belt 39, and solenoids 44A, 44B are housed within door 49. When hinged door 49 is closed and locked into place via locking mechanism 45 (as shown in FIG. 3), rollers 36A, 36B disposed on door 49 abut rollers 37A, 37B. When hinged door 49 is open (as shown in FIG. 4) rollers 37A, 37B are not biased against rollers 36A, 36B.

Figure 5:
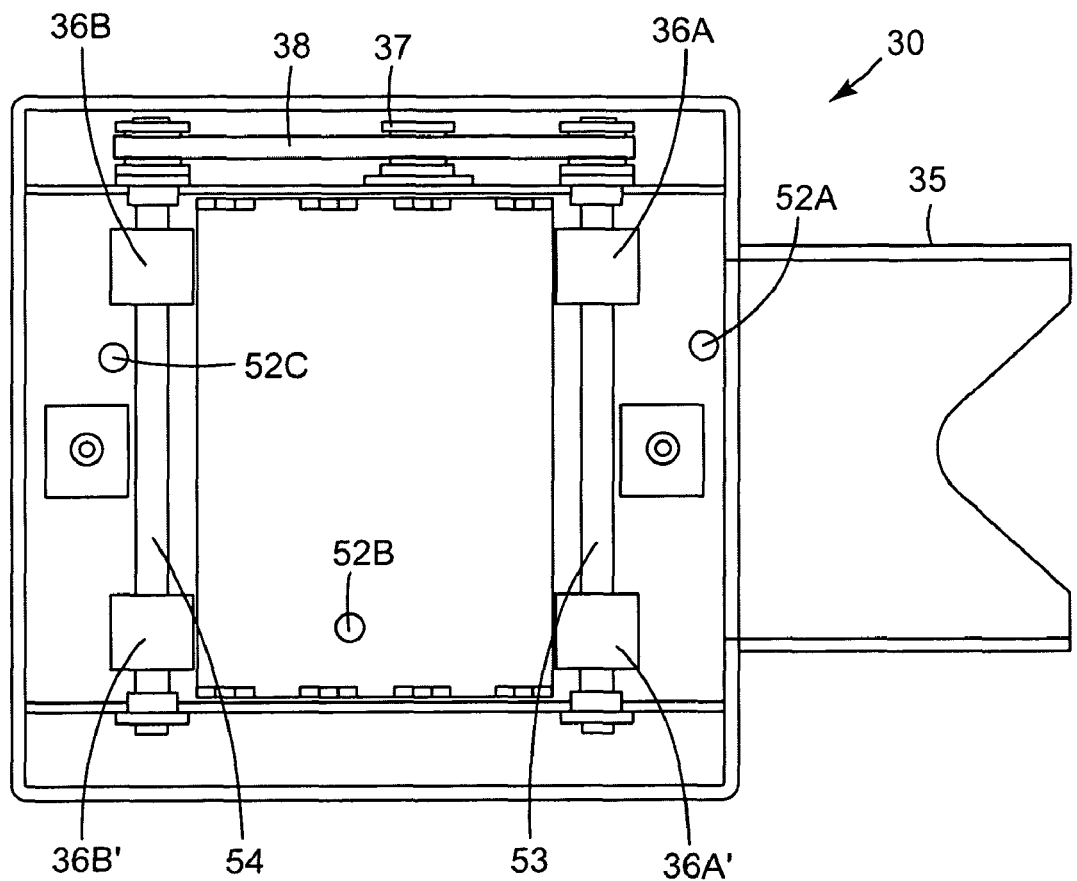
FIG. 5 is a cross-sectional front view of the biological scanner illustrated in FIGS. 3 and 4.

FIG. 5 is a cross-sectional front view of biological scanner 30 illustrating a sensor arrangement that facilitates automated intake of biological growth plates. In particular, biological scanner includes a set of sensors 52A, 52B, 52C that detect positioning of a biological growth plate and automate movement of rollers 36A, 36A', 36B, 36B' and actuator 47 (FIG. 3) in order to facilitate positioning of the growth plate for imaging. Rollers 36A and 36A' may be driven along shaft 53 and rollers 36B and 36B' may be driven along shaft 54. Sensors 52 may be disposed on door 49 or adjacent platen 41. Sensors 52 may comprise optical sensors, or any other type of sensor capable of sensing a growth plate.

When a growth plate is inserted into biological scanner 30 along guiding mechanism 35, first sensor 52A detects the presence of the growth plate and causes motor 38 to drive rollers 36A, 36A', 36B, 36B' via belt 39 in order to draw the growth plate into biological scanner 30. When second sensor 52B detects the growth plate, movement of motor 38 is temporality terminated and solenoids 44A, 44B cause actuator 47 to press the growth plate against platen 41 (see FIG. 3). In particular, second sensor 52B corresponds to a first desirable scanning position of growth plate, e.g., a location where indicia 19 (FIG. 1) of growth plate 12 can be imaged.

Once one or more images of indicia 19 are generated, solenoids 44A, 44B cause actuator 47 to release the growth plate from platen 41. Again, the images of indicia 19 can be used to identify growth plate 12 and facilitate selection of a counting algorithm useful for the identified plate. Motor 38 drives rollers 36A, 36A', 36B, 36B' via belt 39 in order to draw the growth plate further into biological scanner 30. When third sensor 52C detects the growth plate, movement of motor 38 is again terminated and solenoids 44A, 44B cause actuator 47 to press the growth plate against platen 41 (see FIG. 3). In particular, third sensor 52C corresponds to a second desirable scanning position of growth plate 12, e.g., a location where growth area 17 (FIG. 1) of growth plate 12 can be imaged.

In other words, sensors 52A-52C control the processing flow through biological scanner 30. First sensor 52A detects the growth plate and initiates the process of drawing growth plate 12 into biological sensor. Second sensor 52B detects growth plate 12 at a first scanning position and causes imaging to occur. After imaging, growth plate 12 is drawn further into biological scanner 30. Third sensor 52C then detects growth plate 12 at a second scanning position and causes imaging to occur again. Growth plate 12 is then ejected from biological scanner 30. Numerous other sensor arrangements could also be defined. In general, the set of sensors 52 facilitate automated intake and processing of biological growth plates by detecting the location of a growth plate and causing actions to occur at proper times so that desired images of the growth plate can be generated, including an image of indicia carried by the growth plate and an image of the growth area of the growth plate. In other embodiments, however, imaging device 32 (FIG. 3) may be used to facilitate the detection and positioning of the growth plate, instead of sensors.

Figure 6A:
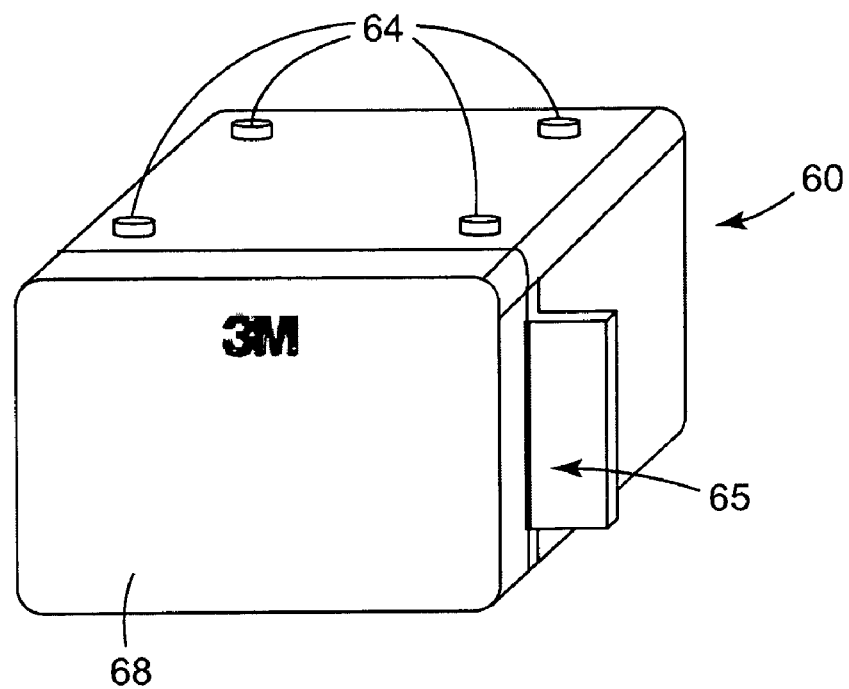
FIGS. 6A and 6B are perspective views collectively illustrating a biological scanner that includes sets of footings disposed on different sides of the scanner.
Figure 6B:
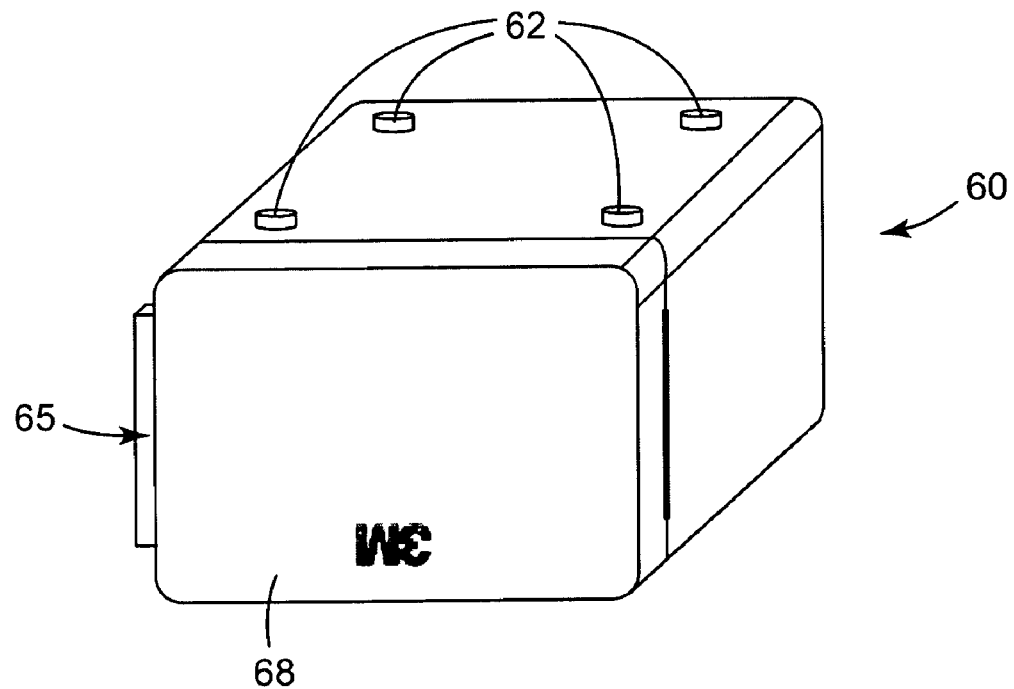

FIGS. 6A and 6B are perspective views collectively illustrating a biological scanner 60 that includes another useful feature. In particular, biological scanner 60 includes a first set of footings 62 disposed on a first side of scanner 60 and a second set of footings 64 disposed on a second side of scanner 60. In this example, the first set of footings 62 are disposed on a bottom side and the second set of footings 64 are disposed on a top side of scanner 60. However, other sides of the scanner could alternatively or additionally have footings.

In accordance with this aspect of the invention, the insertion slot 65 that receives a biological growth plate is disposed on a right side of scanner 60 when scanner 60 is positioned on the first set of footings 62 and a front side 68 of scanner 60 is facing a user (as shown in FIG. 6A). The insertion slot 65 is disposed on a left side of scanner 60 when scanner 60 is positioned on the second set of footings 64 and the front side 68 of scanner 60 is facing the user (as shown in FIG. 6B). In this manner, footings disposed on various sides of scanner 60 can facilitate selective positioning of scanner 60 in inverted orientations for simplified use by right-handed or left-handed users In other words, scanner 60 can be placed "right side-up" or "upside-down," depending on the desired orientation of slot 65. In this manner, footings can be disposed on various sides of scanner 60 to facilitate flexibility in terms of the input and output locations of the scanner. A user may position scanner 60 on a given set of footings 62 or 64 based on the user's preferences or the work environment in which scanner 60 is used. Footings on a back side of scanner may also be desirable for some applications. In this case, if scanner was positioned on footings disposed on its back side, front side 68 would be facing upward and slot 65 would be oriented on an uppermost side of scanner 60.

Figure 7:
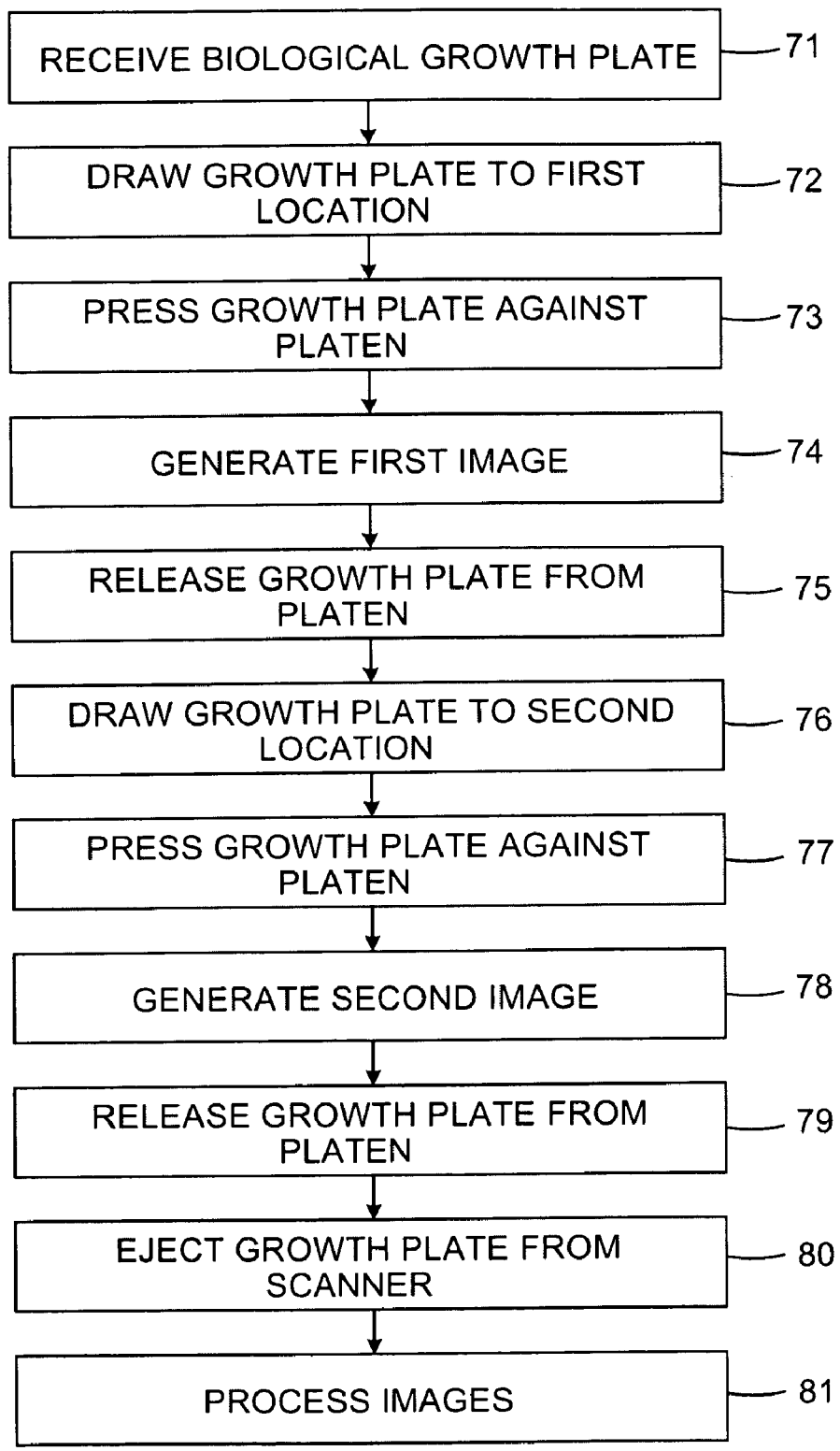
FIG. 7 is a flow diagram illustrating operation of an exemplary biological scanner in accordance with an embodiment of the invention.

FIG. 7 is a flow diagram illustrating operation of an exemplary biological scanner in accordance with an embodiment of the invention. FIG. 7 will be explained with reference to biological scanner 30 of FIGS. 3-5.

Biological scanner 30 receives a biological growth plate (71). For example, a user may insert the biological growth plate into biological scanner 30 between guide mechanism 35 and actuator 47. Upon detection by first sensor 52A, one or more of rollers 36, 37 draw the growth plate to a first location (72), e.g., corresponding to second sensor 52B. Actuator 47 presses the growth plate against platen 41 (73), and biological scanner 30 generates a first image of the biological growth plate (74). For example, illuminators 33A, 33B and possibly back illuminators 42 that may for part of actuator 47 can illuminate the growth plate and imaging device 32 can generate one or more images.

Actuator 47 then releases the growth plate from platen 41 (75). Rollers 36, 37 draw the growth plate to a second location (76), e.g., corresponding to third sensor 52C. Actuator 47 presses the growth plate against platen 41 (77), and biological scanner 30 generates a second image of the biological growth plate (78). By way of example, the first image may correspond to an image of indicia on the growth plate and the second image may correspond to an image of a growth area on the growth plate.

Actuator 47 then releases the growth plate from platen 41 (79), and rollers 36, 37 eject the growth plate from scanner 30 (80). The images are then processed (81). In particular, the images are processed to count bacterial colonies on the growth plate. In one example, the images are internally processed within biological scanner 30 via an internal processor (not shown). In that case, biological scanner 30 would display or otherwise output bacterial counts. In another example, the generated images can be sent to an external computer for processing. In that case, the external computer would display or otherwise output bacterial counts.

A number of embodiments of a biological scanner have been described. For example, sensor arrangements have been described which facilitate sensing and positioning of the growth plate in a plurality of locations for imaging. Automated transport mechanisms and positioning actuators are also described for automating the intake and positioning of a growth plate inside a biological scanner. Additional embodiments are directed to features such as a hinged door that facilitates access to the scanner, and footings disposed on various sides of the scanner to facilitate flip-over of the scanner for simplified use by right-handed or left-handed users.

Nevertheless, various modifications may be made without departing from the spirit and scope of the invention. For example, one or more features described herein may be used with or without other described features. Also, in some embodiments, the imaging device may be used to detect positioning of the growth plate. In that case, one or more of sensors may be eliminated. These and other embodiments are within the scope of the following claims.

The invention claimed is:

1. A biological scanner for scanning a biological growth plate, comprising:
an imaging device to generate an image of the biological growth plate;
a transport mechanism to draw the biological growth plate into the scanner such that the growth plate is positioned in the focal plane of the imaging device, wherein the transport mechanism comprises a sensor to facilitate positioning of the biological growth plate;
a first slot formed in a first side of the scanner for receiving the biological growth plate; and
a second slot formed in a second side of the scanner for ejecting the biological growth plate.

2. The biological scanner of claim 1, wherein the transport mechanism comprises a set of rollers to draw the biological growth plate into the scanner.

3. The biological scanner of claim 2, wherein the biological scanner further comprises a hinged door, wherein the set of rollers includes a first subset of rollers disposed on the door and a second subset of rollers that abut the first subset of the rollers when the hinged door is closed.

4. The biological scanner of claim 1, wherein the transport mechanism comprises a sensor to detect that the biological growth plate is drawn into a scanning position.

5. The biological scanner of claim 1, further comprising a processor that counts biological agents in the plate based on the image.

6. The biological scanner of claim 1, further comprising:
a first illumination device to illuminate a top side of the biological growth plate; and
a second illumination device to illuminate a bottom side of the biological growth plate.

7. The biological scanner of claim 1, further comprising:
a first set of footings on a first side of the biological scanner; and
a second set of footings on a second side of the biological scanner such that the biological scanner can be positioned on either of the first or second set of footings.

8. A biological scanning system comprising:
a biological scanner comprising:
an imaging device,
a transport mechanism to draw the biological growth plate into the scanner such that the growth plate is positioned in the focal plane of the imaging device, wherein the transport mechanism comprises a sensor to facilitate positioning of the biological growth plate;
a first slot formed in a first side of the scanner for receiving the biological growth plate; and
a second slot formed in a second side of the scanner for ejecting the biological growth plate; and
a computer coupled to the biological scanner and including a processor that counts biological agents in the biological growth plate based on the image.

9. A method comprising:
providing a biological growth plate and a biological scanner;
receiving the biological growth plate through a first slot of the biological scanner;
drawing the plate to a scanning position within the scanner, wherein a sensor facilitates positioning of the biological growth plate; and
generating one or more images of the growth plate at the scanning position; and
ejecting the biological growth plate out a second slot in the biological scanner.

10. The method of claim 9, further comprising:
providing a processor to analyze or view images; and
processing the one or more images;
wherein processing the one or more images comprises analyzing the one or more images of the biological growth plates comprises processing the images according to a selected image processing profile.

11. The method of claim 9, further comprising:
providing a processor to analyze or view images; and
processing the one or more images;
wherein processing the one or more images comprises analyzing or viewing the images.

12. The method of claim 11, wherein processing the one or more images comprises viewing the images.

13. The method of claim 11, wherein processing the one or more images comprises analyzing the images.

14. The method of claim 13, wherein analyzing the one or more images comprises generating a bacterial colony count.

15. The method of claim 13, wherein analyzing the one or more images comprises identifying the biological growth plate.

16. The method of claim 13, wherein analyzing the one or more images comprises combining more than one image.

17. The method of claim 16, wherein analyzing the one or more images comprises generating a bacterial colony count.

* * * * *